(12) United States Patent
Aliamiri

(10) Patent No.: US 11,185,284 B2
(45) Date of Patent: Nov. 30, 2021

(54) WEARABLE ELECTROCARDIOGRAM DEVICE

(71) Applicant: Samsung Electronics Co., Ltd., Suwon-si (KR)

(72) Inventor: Alireza Aliamiri, San Jose, CA (US)

(73) Assignee: Samsung Electronics Co., Ltd., Suwon-si (KR)

( * ) Notice: Subject to any disclaimer, the term of this patent is extended or adjusted under 35 U.S.C. 154(b) by 308 days.

(21) Appl. No.: 16/283,569

(22) Filed: Feb. 22, 2019

(65) Prior Publication Data

US 2020/0205732 A1    Jul. 2, 2020

Related U.S. Application Data

(60) Provisional application No. 62/787,716, filed on Jan. 2, 2019.

(51) Int. Cl.
| | |
|---|---|
| *A61B 5/25* | (2021.01) |
| *A61B 5/00* | (2006.01) |
| *H01R 13/03* | (2006.01) |
| *H01R 13/04* | (2006.01) |
| *A61B 5/339* | (2021.01) |

(52) U.S. Cl.
CPC .......... *A61B 5/6802* (2013.01); *A61B 5/0006* (2013.01); *A61B 5/25* (2021.01); *A61B 5/339* (2021.01); *H01R 13/03* (2013.01); *H01R 13/04* (2013.01); *H01R 2201/12* (2013.01)

(58) Field of Classification Search
CPC .......... A61B 5/0006; A61B 5/25; A61B 5/339; A61B 5/6802; H01R 13/03; H01R 13/04; H01R 13/6277; H01R 2201/12
See application file for complete search history.

(56) References Cited

U.S. PATENT DOCUMENTS

| | | | |
|---|---|---|---|
| 9,277,867 B2 | 3/2016 | Kurzweil et al. | |
| 9,662,030 B2 | 5/2017 | Thng et al. | |
| 9,913,591 B2 | 3/2018 | Lapetina et al. | |
| 10,070,798 B2 | 9/2018 | Korkala et al. | |
| 2003/0105403 A1* | 6/2003 | Istvan | A61B 5/282 600/509 |
| 2008/0287769 A1* | 11/2008 | Kurzweil | A61B 5/6823 600/388 |
| 2017/0127966 A1 | 5/2017 | Wu et al. | |
| 2017/0311886 A1 | 11/2017 | Chausiaux et al. | |
| 2018/0020937 A1 | 1/2018 | Chou | |
| 2018/0138616 A1 | 5/2018 | Dumont | |

* cited by examiner

*Primary Examiner* — George Manuel
(74) *Attorney, Agent, or Firm* — Lewis Roca Rothgerber Christie LLP

(57) ABSTRACT

A clip configured to be coupled to an electrocardiogram sensor unit. The clip includes an electrically conductive material having a first surface and a second surface opposite the first surface. The clip also includes electrical insulation coupled to the second surface of the electrically conductive material, and an electrode defined by an exposed portion of the first surface of the electrically conductive material. The clip may be flexible or substantially rigid.

18 Claims, 6 Drawing Sheets

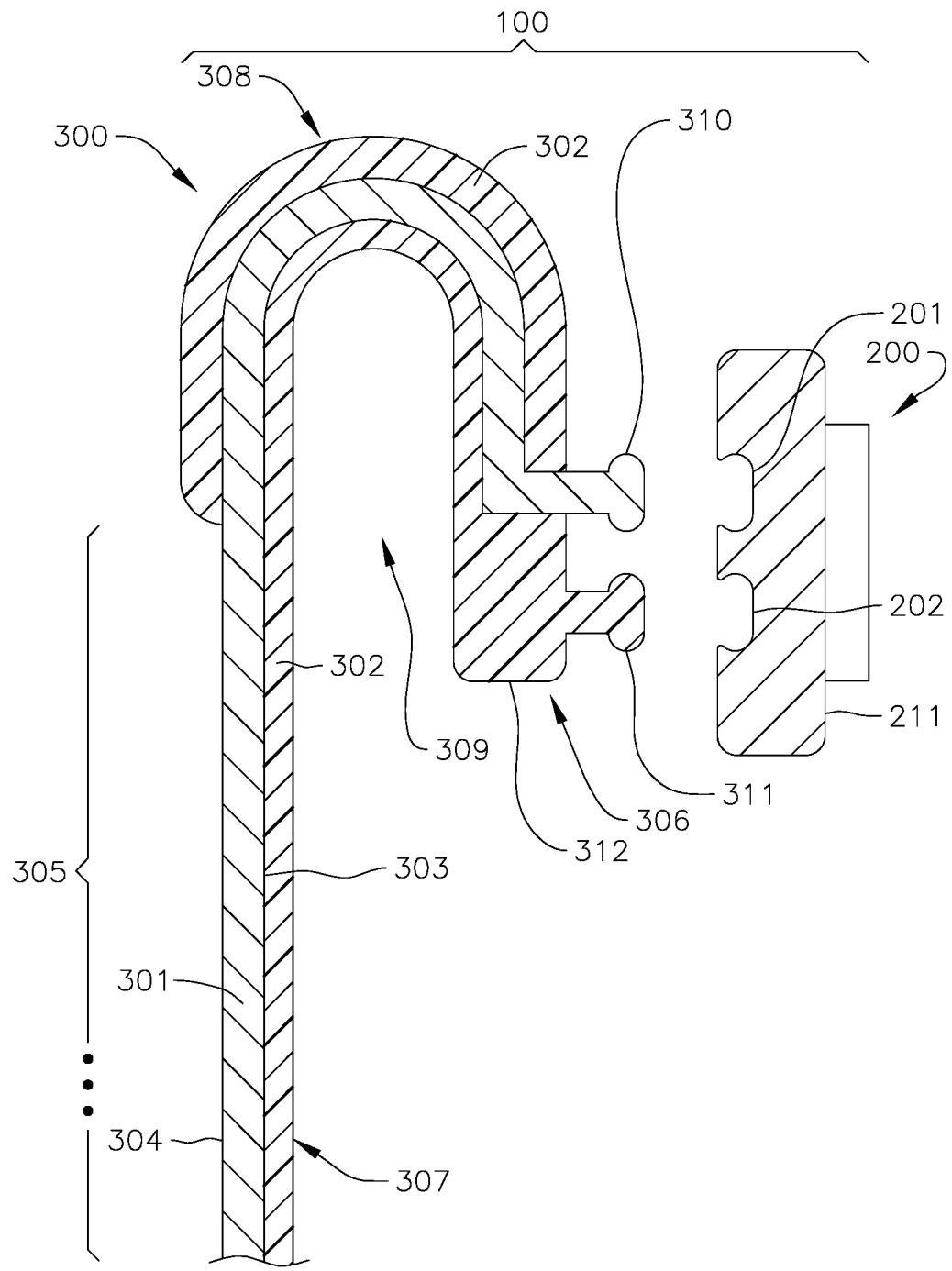

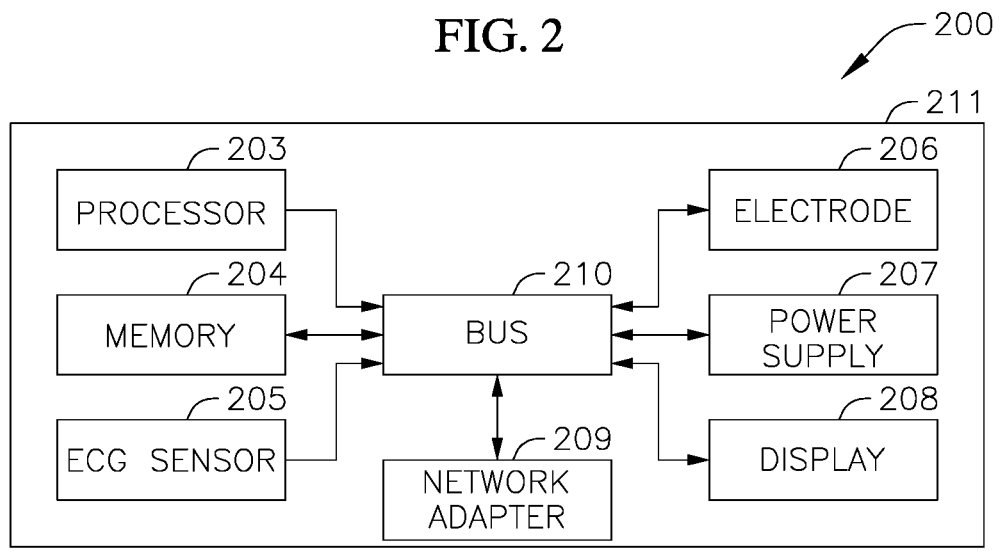
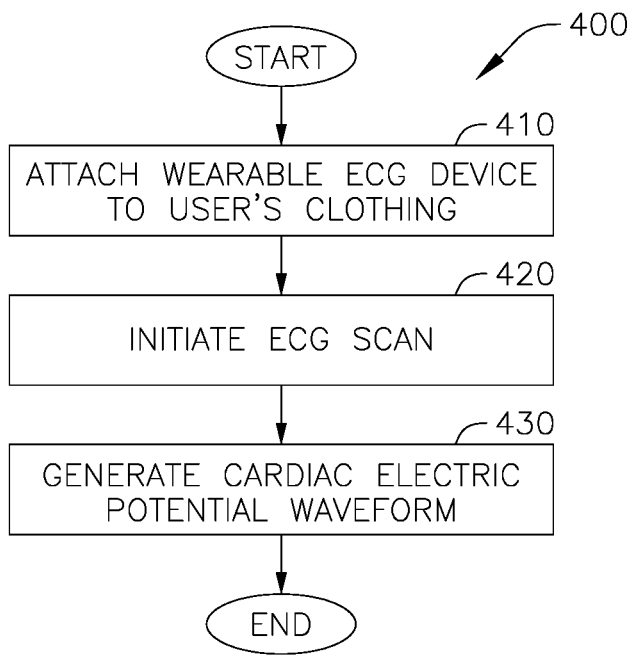

WEARABLE ELECTROCARDIOGRAM DEVICE

CROSS-REFERENCE TO RELATED APPLICATION

The present application claims priority to and the benefit of U.S. Provisional Application No. 62/787,716, filed Jan. 2, 2019, the entire content of which is incorporated herein by reference.

FIELD

The present disclosure relates generally to wearable electrocardiogram devices and methods of performing electrocardiogram scans.

BACKGROUND

An electrocardiogram (ECG) measures electrical activity of the heart, which can be utilized to diagnose many cardiovascular related abnormalities. To perform an ECG scan, at least two electrodes are required and the human body needs to close or complete a circuit between these two electrodes. In some related art ECG devices, the electrodes are connected to the left and rights hands of the user or the left and right leg of the user to create the circuit between the electrodes. Additionally, current ECG devices are configured to perform either continuous ECG monitoring or event ECG monitoring. Continuous ECG monitoring devices perform the ECG scan automatically and include electrodes affixed to the user's skin, such as a Holter monitor in which electrodes are adhered to the user's chest or a chest strap worn around the user's chest. However, such continuous ECG monitoring devices are inconvenient because the electrodes are attached to the user's body, such as by adhesives. Event ECG monitoring devices require a user to actively initiate the ECG scan and include ECG watches. However, related art event ECG monitoring devices are inconvenient because they typically interfere with a user's activities. For instance, a related art ECG watch worn on a user's left hand requires the user to place their right hand on the watch during the duration of the ECG scan, which is typically 30 seconds to one minute, and thus ECG watches severely restrict the activities the user can perform with his or her hands during the ECG scan.

SUMMARY

The present disclosure is directed to various embodiments of a clip configured to be coupled to an electrocardiogram sensor unit. In one embodiment, the clip includes an electrically conductive material having a first surface and a second surface opposite the first surface. The clip also includes electrical insulation coupled to the second surface of the electrically conductive material, and an electrode defined by an exposed portion of the first surface of the electrically conductive material.

The clip may be flexible, and the electrically conductive material may include an electrically conductive fabric.

The clip may be substantially rigid, and the clip may also include electrical insulation coupled to the second surface of the electrically conductive material.

The electrical insulation may cover a portion of the first surface of the electrically conductive material.

The electrical insulation may cover an entirety of the second surface of the electrically conductive material.

The clip may also include at least one electrically conductive connector pin coupled to the electrically conductive material. The connector pin is configured to be detachably coupled to the electrocardiogram sensor unit.

The clip may also include at least one insulator connector pin coupled to the electrical insulation. The insulator connector pin is configured to be detachably coupled to the electrocardiogram sensor unit.

The electrically conductive pin and the insulator connector pin may be proximate to a first end of the clip, and the exposed portion of the electrically conductive material may be at a second end of the clip opposite the first end.

When the clip is coupled to the electrocardiogram sensor unit, the exposed portion of the electrically conductive material may face away from the electrocardiogram sensor unit.

The clip may have a shape including a first leg, a second leg, and a rounded portion connecting the first leg to the second leg.

The present disclosure is also directed to various embodiments of a wearable electrocardiogram device. In one embodiment, the wearable electrocardiogram device includes an electrocardiogram sensor unit including a processor, nonvolatile memory, a power supply, an electrocardiogram sensor, and a first electrode. The wearable electrocardiogram device also includes a clip configured to be coupled to the electrocardiogram sensor unit. The clip includes an electrically conductive material having a first surface and a second surface opposite the first surface, and a second electrode defined by an exposed portion of the first surface of the electrically conductive material.

The clip may be flexible, and the electrically conductive material may include an electrically conductive fabric.

The clip may be substantially rigid, and the clip may also include electrical insulation coupled to the second surface of the electrically conductive material.

The nonvolatile memory may include instructions stored therein which, when executed by the processor, cause the electrocardiogram sensor unit to transmit an electrical signal from the power supply to the first and second electrodes and cause the electrocardiogram sensor to generate a cardiac electrical potential waveform from a signal received by the first and second electrodes in response to the electrical signal transmitted by the first and second electrodes.

The clip may also include at least one electrically conductive connector pin coupled to the electrically conductive material and at least one insulator connector pin coupled to the electrical insulation. The electrocardiogram sensor unit may include at least one first receptacle configured to receive the at least one electrically conductive connector pin and at least one second receptacle configured to receive the at least one insulator connector pin.

The at least one electrically conductive pin and the at least one insulator connector pin may be proximate to a first end of the clip, and the exposed portion of the electrically conductive material may be at a second end of the clip opposite the first end.

When the clip is coupled to the electrocardiogram sensor unit, the exposed portion of the electrically conductive material may face away from the electrocardiogram sensor unit.

The clip may have a shape including a first leg, a second leg, and a rounded portion connecting the first leg to the second leg.

The present disclosure is also directed to various methods of performing an electrocardiogram scan of a user with a wearable electrocardiogram device including an electrocardiogram sensor unit and a clip coupled to the electrocardiogram sensor unit. In one embodiment, the method includes attaching the clip of the wearable electrocardiogram device to an article of clothing worn by the user. The clip includes a first electrode and the electrocardiogram sensor unit includes a second electrode. The method also includes initiating the electrocardiogram scan, which includes transmitting, from the electrocardiogram sensor unit, an electrical signal through the first and second electrodes and the user. The method also includes generating a cardiac electric potential waveform from a signal received by the first and second electrodes in response to the electrical signal transmitted by the electrocardiogram sensor unit.

Generating the cardiac electric potential waveform may include at least one of displaying a visual representation of the cardiac electric potential waveform on a display of the electrocardiogram sensor unit, storing data representative of the electric potential waveform in memory of the electrocardiogram sensor unit, and transmitting data associated with the electric potential waveform to an electronic device.

This summary is provided to introduce a selection of features and concepts of embodiments of the present disclosure that are further described below in the detailed description. This summary is not intended to identify key or essential features of the claimed subject matter, nor is it intended to be used in limiting the scope of the claimed subject matter. One or more of the described features may be combined with one or more other described features to provide a workable device.

BRIEF DESCRIPTION OF THE DRAWINGS

These and other features and advantages of embodiments of the present disclosure will become more apparent by reference to the following detailed description when considered in conjunction with the following drawings. In the drawings, like reference numerals are used throughout the figures to reference like features and components. The figures are not necessarily drawn to scale.

FIGS. 1A-1B are an exploded perspective view and an exploded side view, respectively, of a wearable electrocardiogram device including a clip and an electrocardiogram sensor unit according to one embodiment of the present disclosure;

FIG. 2 is a block diagram of the embodiment of the electrocardiogram sensor unit illustrated in FIGS. 1A-1B;

FIG. 4 is an example cardiac waveform measured by the embodiment of the wearable electrocardiogram device of FIGS. 1A-1B.

DETAILED DESCRIPTION

Figure 1A:
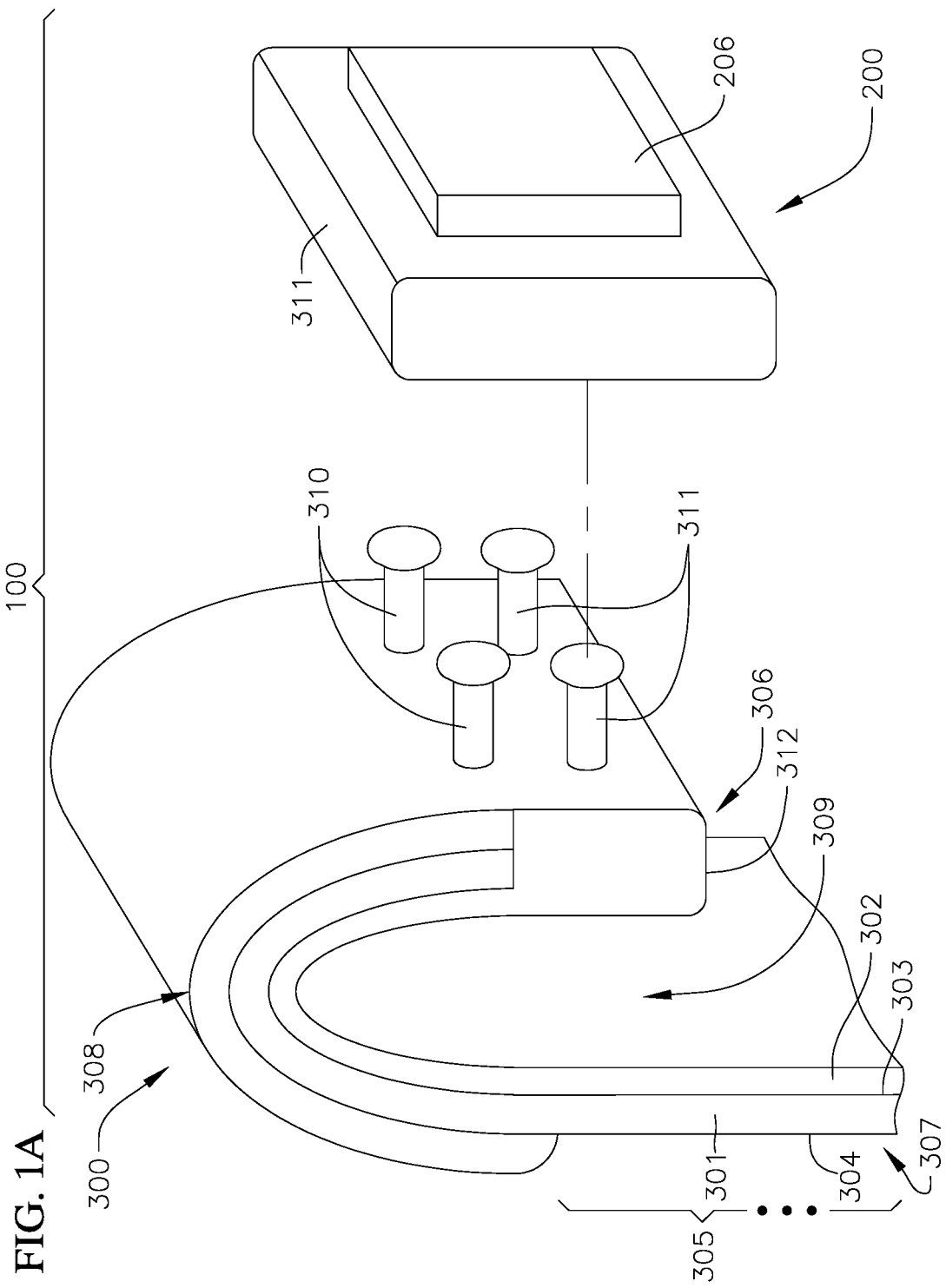

The present disclosure is directed to various embodiments of a wearable electrocardiogram (ECG) device. The ECG device according to various embodiments of the present disclosure includes an ECG sensor unit and a clip configured to be coupled to the ECG sensor unit. The clip is configured to be attached to a user's article of clothing, such as a shirt or a pair of pants, and the clip includes an electrode configured to remain in contact with a portion of the user's skin (e.g., the user's torso or chest). The clip may be either a flexible clip suitable, for instance, to attach to the user's pair of pants, or a rigid or substantially rigid clip suitable, for instance, to attach to the user's shirt. The ECG sensor unit also includes an electrode. An ECG scan may be initiated when the user's body closes an electrical circuit between the electrode of the clip and the electrode of the ECG sensor unit. Accordingly, because the electrode of the clip remains in contact with the user's body, the ECG device is configured to enable a user to initiate an ECG scan with only one hand, unlike related art ECG devices, such as smart watches, that require the use of both of the user's hands to initiate an ECG scan. In this manner, the ECG device according to various embodiments of the present disclosure is configured to perform an ECG scan semi-continuously, and the ECG devices of the present disclosure are configured to enable a user to continue various activities during the ECG scan.

Hereinafter, example embodiments will be described in more detail with reference to the accompanying drawings, in which like reference numbers refer to like elements throughout. The present invention, however, may be embodied in various different forms, and should not be construed as being limited to only the illustrated embodiments herein. Rather, these embodiments are provided as examples so that this disclosure will be thorough and complete, and will fully convey the aspects and features of the present invention to those skilled in the art. Accordingly, processes, elements, and techniques that are not necessary to those having ordinary skill in the art for a complete understanding of the aspects and features of the present invention may not be described. Unless otherwise noted, like reference numerals denote like elements throughout the attached drawings and the written description, and thus, descriptions thereof may not be repeated.

In the drawings, the relative sizes of elements, layers, and regions may be exaggerated and/or simplified for clarity. Spatially relative terms, such as "beneath," "below," "lower," "under," "above," "upper," and the like, may be used herein for ease of explanation to describe one element or feature's relationship to another element(s) or feature(s) as illustrated in the figures. It will be understood that the spatially relative terms are intended to encompass different orientations of the device in use or in operation, in addition to the orientation depicted in the figures. For example, if the device in the figures is turned over, elements described as "below" or "beneath" or "under" other elements or features would then be oriented "above" the other elements or features. Thus, the example terms "below" and "under" can encompass both an orientation of above and below. The device may be otherwise oriented (e.g., rotated 90 degrees or at other orientations) and the spatially relative descriptors used herein should be interpreted accordingly.

It will be understood that, although the terms "first," "second," "third," etc., may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present invention.

It will be understood that when an element or layer is referred to as being "on," "connected to," or "coupled to" another element or layer, it can be directly on, connected to, or coupled to the other element or layer, or one or more intervening elements or layers may be present. In addition, it will also be understood that when an element or layer is referred to as being "between" two elements or layers, it can be the only element or layer between the two elements or layers, or one or more intervening elements or layers may also be present.

The terminology used herein is for the purpose of describing particular embodiments and is not intended to be limiting of the present invention. As used herein, the singular forms "a" and "an" are intended to include the plural forms as well, unless the context clearly indicates otherwise. It will be further understood that the terms "comprises," "comprising," "includes," and "including," when used in this specification, specify the presence of the stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list.

As used herein, the term "substantially," "about," and similar terms are used as terms of approximation and not as terms of degree, and are intended to account for the inherent variations in measured or calculated values that would be recognized by those of ordinary skill in the art. Further, the use of "may" when describing embodiments of the present invention refers to "one or more embodiments of the present invention." As used herein, the terms "use," "using," and "used" may be considered synonymous with the terms "utilize," "utilizing," and "utilized," respectively. Also, the term "exemplary" is intended to refer to an example or illustration.

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and/or the present specification, and should not be interpreted in an idealized or overly formal sense, unless expressly so defined herein.

With reference now to FIGS. 1A-1B, a wearable electrocardiogram (ECG) device 100 according to one embodiment of the present disclosure includes an ECG sensor unit 200 and a clip 300 coupled to, or configured to be coupled to, the ECG sensor unit 200.

In the illustrated embodiment, the clip 300 includes an electrically conductive material 301 and electrical insulation 302 covering a portion of the electrically conductive material 301. In the illustrated embodiment, the electrical insulation 302 covers an entirety of a front surface 303 of the electrically conductive material 301 (e.g., no portion of the front surface 303 of the electrically conductive material 301 is exposed) and the electrical insulation 302 partially covers a rear surface 304 of the electrically conductive material 301 opposite the front surface 303 such that a portion 305 of the rear surface 304 of the electrically conductive material 301 is exposed by the electrical insulation 302. In one or more embodiments, the entirety or substantially the entirety of the rear surface 304 of the electrically conductive mterial 301 may be exposed (e.g., the electrical insulation 302 may cover no portion or substantially no portion of the rear surface 304 of the electrically conductive material 301). In use, the exposed portion 305 of the rear surface 304 of the electrically conductive material 301 is configured to contact a user's skin (e.g., at the user's torso) and function as an electrode during an electrocardiogram scan operation.

In one or more embodiments, the clip 300 may be flexible or rigid (or substantially rigid). In one or more embodiments in which the clip 300 is flexible, the electrically conductive material 301 may be a flexible, electrically conductive fabric. In one or more embodiments in which the clip 300 is flexible, the clip 300 may be provided without the insulation 302, although in one or more embodiments in which the clip 300 is flexible, the clip 300 may be provided with flexible insulation 302.

In the illustrated embodiment, the clip 300 has a generally inverted U-shape. In the illustrated embodiment, the inverted U-shape includes a first leg 306, a second leg 307, and a curved portion 308 connecting ends of the first and second legs 306, 307 together. Additionally, in the illustrated embodiment, the second leg 307 is longer than the first leg 306, although in one or more embodiments, the first and second legs 306, 307 may have the same or substantially the same length. Together, the first and second legs 306, 307 and the curved portion 308 define a cavity 309 configured to accommodate, for example, a portion of an article of clothing (e.g., the waistband of a pair of pants or the placket of a shirt) during use. In one or more embodiments, the clip 300 may have any other suitable shape depending, for instance, on the location of the user that the clip 300 is intended to be attached. Additionally, in the illustrated embodiment, the front surface 303 of the electrically conductive material 301 faces inward toward the cavity 309, and the rear surface 304 of the electrically conductive material 301 faces outward away from the cavity 309. Accordingly, in one or more embodiments, the cavity 309, which is configured to receive the user's article of clothing, is lined with the electrical insulation 302. Furthermore, in the illustrated embodiment, the exposed portion 305 of the rear surface 304 of the electrically conductive material 301, which is configured to contact a user's skin and function as an electrode during an electrocardiogram scan operation, is provided along the longer, second leg of the clip 300.

In one or more embodiments, the clip 300 may be configured to be detachably coupled to the ECG sensor unit 200. In the illustrated embodiment, the clip 300 includes an electrically conductive connector pin 310 at one end of the electrically conductive material 301, and an electrical insulator connector pin 311 at one end of the electrical insulation 302. In the illustrated embodiment, the connector pins 310, 311 are proximate to an end 312 of the first leg 306 of the clip 300 opposite the end at which the curved portion 308 is connected to the first leg 306. Additionally, in the illustrated embodiment, the ECG sensor unit 200 includes a pair of receptacles 201, 202 configured to receive the connector pins 310, 311, respectively, to detachably couple the clip 300 to the ECG sensor unit 200. The detachability of the clip 300 enables the clip 300 to be coupled to a variety of different ECG sensor units (e.g., the wearable ECG device 100 may be upgraded with newer model ECG sensor units without having to replace the clip 300). When the electrically conductive connector pin 310 is received in the corresponding receptacle in the ECG sensor unit 200, the electrically conductive material 301 is electrically coupled to the ECG sensor unit 200, and the electrical components therein, via the electrically conductive connector pin 310. In one or more embodiments, the clip 300 may be provided without the electrical insulator connector pin 311. In one or more embodiments in which the clip 300 is provided without the electrical insulator connector pin 311, the clip 300 may be provided with two or more electrically conductive connector pins coupled to the electrically conductive material 301.

FIG. 2 is a schematic block diagram of the ECG sensor unit 200 according to one embodiment of the present disclosure. In the illustrated embodiment, the ECG sensor unit 200 includes a processor 203, a nonvolatile memory 204, at least one ECG sensor 205, an electrode 206, a power supply 207 (e.g., at least one rechargeable battery), a display 208 configured to display images (e.g., a liquid crystal display (LCD) or an organic light emitting diode (OLED) display), and a network adapter 209 configured to communicate with other electronic devices. In one or more embodiments, the memory 204 may include persistent memory, such as NAND flash memory, for storing data collected and processed ECG sensor unit 200. In the illustrated embodiment, the processor 203, the memory 204, the sensor 205, the electrode 206, the power supply 207, the display 208, and the network adapter 209 communicate with one another over a system bus 210.

The electrode 206 may be exposed on any portion of the ECG sensor unit 200 (e.g., the electrode 206 may be exposed on an outer face or a side of a housing 211 of the ECG sensor unit 200) such that a user may contact, for instance, his or her hand on the electrode 206. When a closed loop circuit is formed with the electrode 305 of the clip 300 and the electrode 206 of the ECG sensor unit 200 (e.g., when the user's torso is in contact with the exposed portion 305 of the rear surface 304 of the electrically conductive material 301, which functions as an electrode, and the user's hand is in contact with the electrode 206 of the ECG sensor unit 200) and an electrical signal is transmitted through one of the electrodes 305, 206, the ECG sensor 205 is configured to measure cardiac electrical potential waveforms (i.e., voltages produced during the contraction of the user's heart). An example of a cardiac electrical potential waveform measured by the ECG sensor 205 is illustrated in FIG. 4.

In one or more embodiments, the ECG sensor unit 200 may be provided without the display 208. Additionally, in one or more embodiments, the ECG sensor unit 200 may be provided without the network adapter 209. In one or more embodiments, the ECG sensor unit 200 may include a universal serial bus (USB) or other connector for connecting the ECG sensor unit 200 to another electronic device.

The term "processor" is used herein to include any combination of hardware, firmware, and software, employed to process data or digital signals. The hardware of a processor may include, for example, application specific integrated circuits (ASICs), general purpose or special purpose central processors (CPUs), digital signal processors (DSPs), graphics processors (GPUs), and programmable logic devices such as field programmable gate arrays (FPGAs). In a processor, as used herein, each function is performed either by hardware configured, i.e., hard-wired, to perform that function, or by more general purpose hardware, such as a CPU, configured to execute instructions stored in a non-transitory storage medium. A processor may be fabricated on a single printed wiring board (PWB) or distributed over several interconnected PWBs. A processor may contain other processors; for example a processor may include two processors, an FPGA and a CPU, interconnected on a PWB.

The memory 204 of the ECG sensor unit 200 stores instructions that, when executed by the processor 203, cause the ECG sensor unit 200 to perform various functions. In one or more embodiments, the instructions stored in the memory 204, when executed by the processor 203, cause the processor 203 to send an electrical signal from the power supply 207 through one of the electrodes 305 or 206. When the user's skin is in contact with both of the electrodes 305, 206 (i.e., a closed circuit is formed with the electrodes 305, 206), the electrical signal transmitted by the ECG sensor unit 200 is configured to pass through the user's body to the other electrode 206 or 305 and then be processed by the ECG sensor 205, which generates a cardiac electrical potential waveform from the received electrical signal, as shown, for instance, in FIG. 4. In one or more embodiments, the memory 204 of the ECG sensor unit 200 may include instructions stored therein which, when executed by the processor 203, cause the memory 204 to save the cardiac electrical waveform and/or cause the display 208 the cardiac electrical waveform on the display 208. In one or more embodiments, the memory 204 of the ECG sensor unit 200 may include instructions stored therein which, when executed by the processor 203, cause the network adapter 209 to wirelessly transmit the cardiac electrical waveform to another electronic device (e.g., a computer, a smartphone, or any other network enabled device).

Figure 3B:
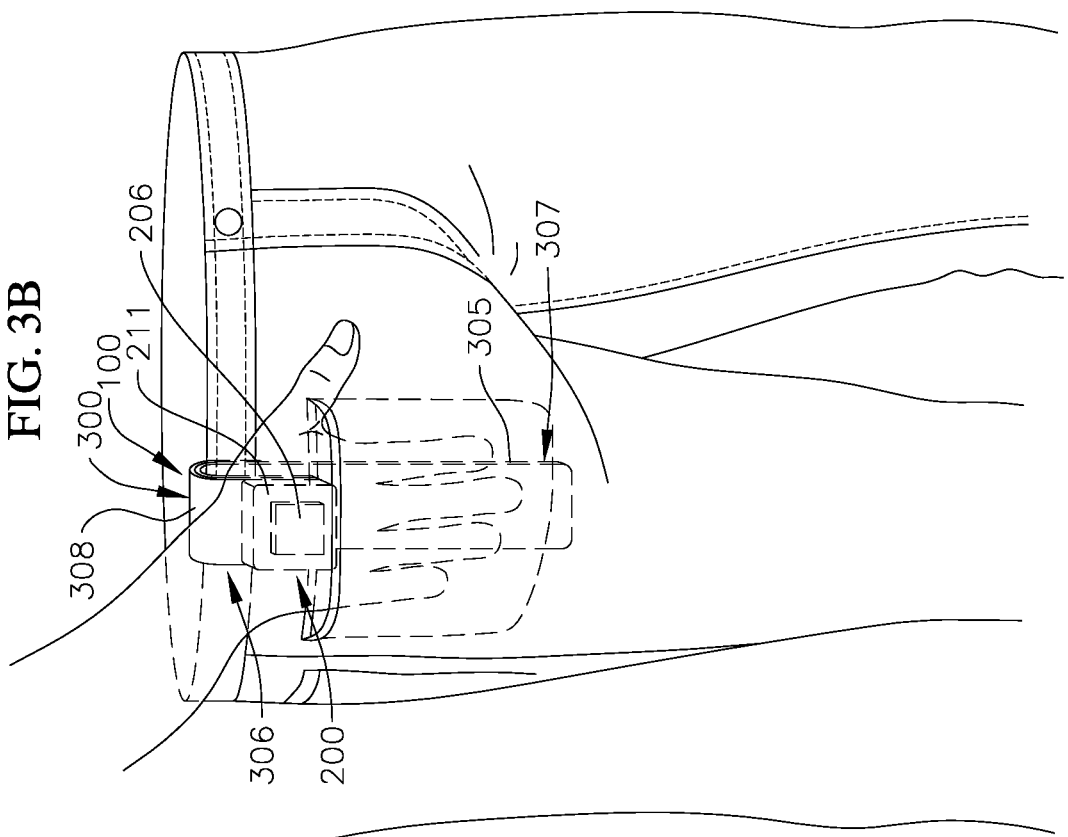
FIGS. 3A-3C are perspective views illustrating use of the embodiment of the wearable electrocardiogram device of FIGS. 1A-1B to perform an EKG scan of a user according to one embodiment of the present disclosure.
Figure 3A:
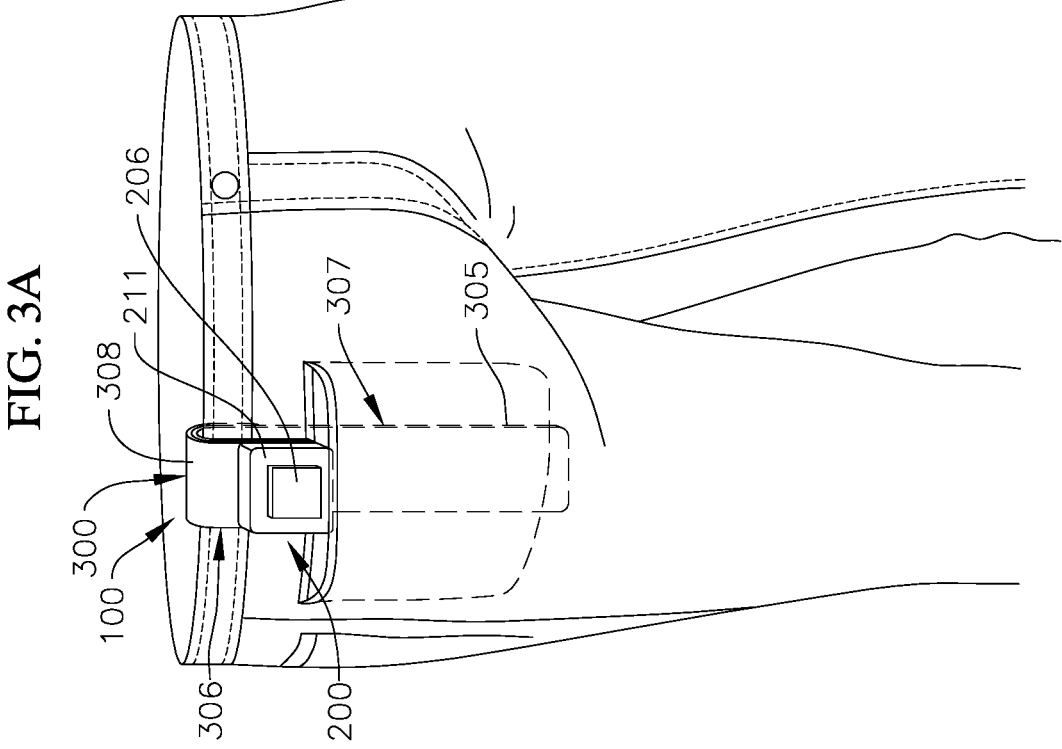

FIGS. 3A-3B are perspective views illustrating a user utilizing the embodiment of the wearable ECG device 100 to perform an ECG scan. In the embodiment illustrated in FIGS. 3A-3B, the clip 300 is attached to the waistband of a pair of pants. In the illustrated embodiment, the second leg 307 of the clip 300 is inserted into the waist opening of the pair of pants and the electrode of the clip 300 (e.g., the exposed portion 305 of the of the rear surface 304 of the electrically conductive material 301), which faces inward toward the user, is in contact with the skin of the user's torso. Additionally, the waistband extends up into the cavity 309 and the curved portion 308 of the clip 300 is supported on the waistband such that the clip 300 overhangs the waistband, and the first leg 306 of the clip 300 extends down from the waistband along the front side of the pair of pants. In one embodiment, the clip 300 may be aligned with a front pocket of the pair of pants. Additionally, in one embodiment, the first leg 306 of the clip 300 may be configured to extend at least partially into the front pocket of the pair of pants. In one embodiment, the first leg 306 of the clip 300 may be configured to extend completely into the front pocket of the pair of pants. In use, the user may initiate an ECG scan by placing his or her hand on the electrode 206 of the ECG sensor unit 200. Because the electrode 206 of the clip 300 is always in contact with the user's torso, the user can initiate an ECG scan by occupying only one of the user's hands, unlike related art ECG devices that occupy both of the user's hands. Additionally, in the embodiment illustrated in FIGS. 3A-3B in which the wearable ECG device 100 is attached to the user's pants, the clip 300 may be flexible (e.g., the electrically conductive material 301 may be a flexible, electrically conductive fabric).

Figure 3C:
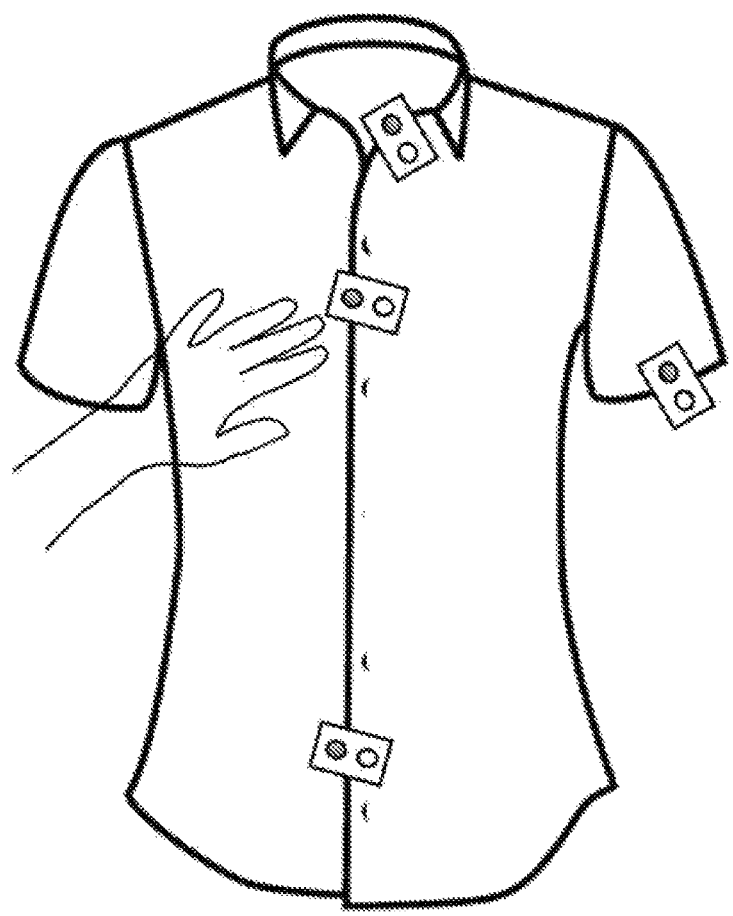

In one or more embodiments, the wearable electrocardiogram device 100 may be connected to any other article of clothing. In the embodiment illustrated in FIG. 3C, the clip 300 is attached to a shirt (e.g., the placket, collar, and/or sleeve of the shirt). For instance, the wearable electrocardiogram device 100 may be attached to the placket of a shirt by, for example, inserting the second leg 307 of the clip 300 through the placket such that the electrode (e.g., the exposed portion 305 of the rear surface 304 of the electrically conductive material 301), which faces inward toward the user, is in contact with the user's chest, the placket extends into the cavity 309, the curved portion 308 of the electrically conductive material 301 extends around the placket, and the first leg 306 of the clip 300, and the ECG sensor unit 200 coupled thereto, is exposed outside of the shirt. In use, the user may initiate an ECG scan by placing his or her hand on the electrode 206 of the ECG sensor unit 200 exposed on the outside of the user's shirt. Moreover, because the electrode 206 of the clip 300 is always in contact with the user's chest, the user can initiate an ECG scan by occupying only one of the user's hands, unlike related art ECG devices that occupy both of the user's hands. Additionally, in the embodiment illustrated in FIG. 3C in which the wearable ECG device 100 is attached to the user's shirt, the clip 300 may be rigid or substantially rigid.

Figure 5:
FIG. 5 is a flowchart illustrating tasks of a method of performing an EKG scan of a user according to one embodiment of the present disclosure.

FIG. 5 is a flowchart illustrating tasks of a method 400 of performing an electrocardiogram scan of a user. In the illustrated embodiment, the method 400 includes a task 410 of attaching a wearable electrocardiogram device including an electrocardiogram sensor unit and a clip coupled to the electrocardiogram (ECG) sensor unit (e.g., the embodiment of the wearable electrocardiogram device 100 illustrated in FIGS. 1A-2) to an article of clothing of a user (e.g., the waistband of the user's pants, as illustrated in FIGS. 3A-3B, or to the placket, collar, or sleeve of the user's shirt). In one or more embodiments, the task 410 of attaching the wearable electrocardiogram device to the article of clothing includes inserting at least a portion of the clip (e.g., the embodiment of the clip 300 illustrated in FIGS. 1A-2) of the wearable electrocardiogram device into the article of clothing. When at least a portion of the clip is inserted into the article of clothing, an electrode of the clip is in contact with the user's skin (e.g., the torso of the user or the chest of the user). Additionally, when the clip is attached to the article of clothing, an electrode of the electrocardiogram sensor unit is exposed outside of the article of clothing (e.g., the electrode may be exposed on the outside of the user's shirt or on the outside of the user's pants). In one or more embodiments, when the clip is attached to the user's pair of pants, the electrode on the ECG sensor unit may extend at least partially into one of the pockets of the pair of pants, as illustrated, for instance, in FIGS. 3A-3B.

In the illustrated embodiment, the method 400 also includes a task 420 of initiating the electrocardiogram scan of the user. In one embodiment, task 420 of initiating the electrocardiogram scan includes the user placing a finger or other portion of one of the user's hands on the electrode of the ECG sensor unit. Because the electrode of the clip is in contact with the user's skin without occupying one of the user's hands, the electrocardiogram scan may be initiated with only one of the user's hands, which enables the user to continue various activities during the ECG scan, unlike related art ECG devices, such as smart watches, that require the use of both of the user's hands to initiate an ECG scan. Moreover, the electrode of the clip, which remains in contact with the user's skin when the clip is connected to the user's article of clothing, enables the ECG scan to be performed semi-continuously, compared to related art continuous monitoring that typically require electrodes to be adhered to the user's body and related art event monitoring that typically requires use of both of the user's hands. When the user's finger or other portion of one of the user's hands is placed on the electrode of the electrocardiogram sensor unit, the user's body closes an electrical circuit or loop between the electrodes. In one or more embodiments, the electrocardiogram sensor unit is configured to detect when the circuit is closed. When the circuit is closed, the electrocardiogram sensor unit is configured to transmit an electrical signal through the electrode of the clip or the electrode of the electrocardiogram sensor unit. The electrical signal transmitted by the ECG sensor unit passes through the user's body and is received by the other electrode (e.g., the electrode of the clip or the electrode of the ECG sensor unit).

In one or more embodiments, the task 420 of performing the ECG scan may occur for any suitable duration, such as 1 minute or approximately 1 minute, although in one or more embodiments the duration of the ECG scan may be less than 1 minute or longer than 1 minute.

In the illustrated embodiment, the method 400 also includes a task 430 of generating a cardiac electric potential waveform from the signal received by the electrodes in response to the electrical signal transmitted by the ECG sensor unit (e.g., the task may include generating the cardiac electric potential waveform illustrated in FIG. 4). In one or more embodiments, the task 430 of generating the cardiac electric potential waveform may be performed by any suitable type or kind of ECG sensor, such as the ECG sensor 205 described above with reference to the embodiment illustrated in FIG. 2. The cardiac electric potential waveform is a measurement of the electrical activity of the user's heart (i.e., voltages produced during the contraction of the user's heart), which may be utilized to diagnose cardiovascular related abnormalities. In one or more embodiments, the task 430 of generating the cardiac electric potential waveform may include a task of displaying a visual representation of the cardiac electric potential waveform (or one or more properties thereof) on a display (e.g., an LCD or LED screen) of the ECG sensor unit, storing data representative of the electric potential waveform in memory (e.g., persistent memory, such as NAND) of the ECG sensor unit, and/or transmitting data associated with the electric potential waveform to another electronic device, such as a computer, a smartphone, or any other network connected device (e.g., transmitting data through a network adapter of the ECG sensor unit).

While this invention has been described in detail with particular references to exemplary embodiments thereof, the exemplary embodiments described herein are not intended to be exhaustive or to limit the scope of the invention to the exact forms disclosed. Persons skilled in the art and technology to which this invention pertains will appreciate that alterations and changes in the described structures and methods of assembly and operation can be practiced without meaningfully departing from the principles, spirit, and scope of this invention, as set forth in the following claims.

What is claimed is:

1. A clip configured to be coupled to an electrocardiogram sensor unit, the clip comprising:
   an electrically conductive material having a first surface and a second surface opposite the first surface;
   an inwardly-facing electrode defined by an exposed portion of the first surface of the electrically conductive material; and
   at least one electrically conductive connector pin coupled to the electrically conductive material and extending outward away from the inwardly-facing electrode, the at least one connector pin configured to be detachably coupled to the electrocardiogram sensor unit,
   wherein the clip is flexible, and wherein the electrically conductive material comprises an electrically conductive fabric.

2. The clip of claim 1, wherein, when the clip is coupled to the electrocardiogram sensor unit, the exposed portion of the electrically conductive material faces away from the electrocardiogram sensor unit.

3. The clip of claim 1, wherein the clip has a shape comprising:
   a first leg;
   a second leg; and a rounded portion connecting the first leg to the second leg.

4. A clip configured to be coupled to an electrocardiogram sensor unit, the clip comprising:
  an electrically conductive material having a first surface and a second surface opposite the first surface;
  electrical insulation coupled to the second surface of the electrically conductive material;
  an inwardly-facing electrode defined by an exposed portion of the first surface of the electrically conductive material;
  at least one electrically conductive connector pin coupled to the electrically conductive material and extending outward away from the inwardly-facing electrode, the at least one connector pin configured to be detachably coupled to the electrocardiogram sensor unit; and
  at least one insulator connector pin coupled to the electrical insulation, the at least one insulator connector pin configured to be detachably coupled to the electrocardiogram sensor unit.

5. The clip of claim 4, wherein the clip is substantially rigid.

6. The clip of claim 5, wherein the electrical insulation covers a portion of the first surface of the electrically conductive material.

7. The clip of claim 5, wherein the electrical insulation covers an entirety of the second surface of the electrically conductive material.

8. The clip of claim 4, wherein the at least one electrically conductive pin and the at least one insulator connector pin are proximate to a first end of the clip, and wherein the exposed portion of the electrically conductive material is at a second end of the clip opposite the first end.

9. A wearable electrocardiogram device comprising:
  an electrocardiogram sensor unit, comprising:
    a processor;
    nonvolatile memory;
    a power supply;
    an electrocardiogram sensor; and
    a first electrode;
  a clip configured to be coupled to the electrocardiogram sensor unit, the clip comprising:
    an electrically conductive material having a first surface and a second surface opposite the first surface; and
    a second electrode defined by an exposed portion of the first surface of the electrically conductive material,
  wherein the first electrode is exposed on an outer surface of the electrocardiogram sensor unit when the electrocardiogram sensor unit is coupled to the clip.

10. The wearable electrocardiogram device of claim 9, wherein the clip is flexible, and wherein the electrically conductive material comprises an electrically conductive fabric.

11. The wearable electrocardiogram device of claim 9, wherein the clip is substantially rigid, and wherein the clip further comprises electrical insulation coupled to the second surface of the electrically conductive material.

12. The wearable electrocardiogram device of claim 11, wherein:
  the clip further comprises at least one electrically conductive connector pin coupled to the electrically conductive material and at least one insulator connector pin coupled to the electrical insulation, and
  the electrocardiogram sensor unit further comprises at least one first receptacle configured to receive the at least one electrically conductive connector pin and at least one second receptacle configured to receive the at least one insulator connector pin.

13. The wearable electrocardiogram device of claim 12, wherein the at least one electrically conductive pin and the at least one insulator connector pin are proximate to a first end of the clip, and wherein the exposed portion of the electrically conductive material is at a second end of the clip opposite the first end.

14. The wearable electrocardiogram device of claim 9, wherein, when the clip is coupled to the electrocardiogram sensor unit, the exposed portion of the electrically conductive material faces away from the electrocardiogram sensor unit.

15. The wearable electrocardiogram device of claim 9, wherein the clip has a shape comprising:
  a first leg;
  a second leg; and
  a rounded portion connecting the first leg to the second leg.

16. A wearable electrocardiogram device comprising:
  an electrocardiogram sensor unit, comprising:
    a processor;
    nonvolatile memory;
    a power supply;
    an electrocardiogram sensor; and
    a first electrode;
  a clip configured to be coupled to the electrocardiogram sensor unit, the clip comprising:
    an electrically conductive material having a first surface and a second surface opposite the first surface; and
    a second electrode defined by an exposed portion of the first surface of the electrically conductive material,
  wherein the nonvolatile memory comprises instructions stored therein which, when executed by the processor, cause the electrocardiogram sensor unit to transmit an electrical signal from the power supply to the first and second electrodes and cause the electrocardiogram sensor to generate a cardiac electrical potential waveform from a signal received by the first and second electrodes in response to the electrical signal transmitted by the first and second electrodes.

17. A method of performing an electrocardiogram scan of a user with a wearable electrocardiogram device comprising an electrocardiogram sensor unit and a clip coupled to the electrocardiogram sensor unit, the method comprising:
  attaching the clip of the wearable electrocardiogram device to an article of clothing worn by the user, the clip comprising a first electrode and the electrocardiogram sensor unit comprising a second electrode;
  initiating the electrocardiogram scan comprising transmitting, from the electrocardiogram sensor unit, an electrical signal through the first and second electrodes and the user; and
  generating a cardiac electric potential waveform from a signal received by the first and second electrodes in response to the electrical signal transmitted by the electrocardiogram sensor unit.

18. The method of claim 17, wherein the generating the cardiac electric potential waveform comprises at least one of displaying a visual representation of the cardiac electric potential waveform on a display of the electrocardiogram sensor unit, storing data representative of the electric potential waveform in memory of the electrocardiogram sensor unit, and transmitting data associated with the electric potential waveform to an electronic device.

* * * * *